US012752035B2

(12) United States Patent
Chen

(10) Patent No.: US 12,752,035 B2
(45) Date of Patent: Oct. 6, 2026

(54) AIR SANITIZATION

(71) Applicant: Singletto Inc., Seattle, WA (US)

(72) Inventor: James Chongchu Chen, Clyde Hill, WA (US)

(73) Assignee: Singletto Inc., Seattle, WA (US)

( * ) Notice: Subject to any disclaimer, the term of this patent is extended or adjusted under 35 U.S.C. 154(b) by 0 days.

(21) Appl. No.: 18/379,863

(22) Filed: Oct. 13, 2023

(65) Prior Publication Data

US 2024/0123108 A1 Apr. 18, 2024

Related U.S. Application Data

(60) Provisional application No. 63/415,902, filed on Oct. 13, 2022.

(51) Int. Cl.
*A61L 9/20* (2006.01)

(52) U.S. Cl.
CPC .......... *A61L 9/205* (2013.01); *A61L 2209/15* (2013.01)

(58) Field of Classification Search
CPC ............................ A61L 9/205; A61L 2209/15
See application file for complete search history.

(56) References Cited

U.S. PATENT DOCUMENTS

| | | | |
|---|---|---|---|
| 2,547,825 | A | 4/1951 | King |
| 2,637,887 | A | 5/1953 | Goodman et al. |
| 3,674,486 | A | 7/1972 | Milgrom |
| 3,817,389 | A | 6/1974 | Weichselbaum |
| 4,059,852 | A | 11/1977 | Crane |
| 4,089,065 | A | 5/1978 | McGee |
| 4,324,005 | A | 4/1982 | Willis |
| 4,382,079 | A | 5/1983 | Marschner |
| 4,395,789 | A | 8/1983 | Bruce |
| 4,402,318 | A | 9/1983 | Swartz |
| 4,685,151 | A | 8/1987 | Kincheloe |
| 4,775,348 | A | 10/1988 | Collins |

(Continued)

FOREIGN PATENT DOCUMENTS

| | | |
|---|---|---|
| AU | 2006341380 B2 | 1/2013 |
| AU | 2013202001 A1 | 4/2013 |

(Continued)

OTHER PUBLICATIONS

Huang et al., "Chitosan and its derivatives as vehicles for drug delivery," Drug Delivery, 2017, vol. 24, No. 2, pp. 108-113.

(Continued)

*Primary Examiner* — Brendan A Hensel

(74) *Attorney, Agent, or Firm* — John W. Branch; Branch Partners PLLC

(57) ABSTRACT

An apparatus and method to actively purify and sanitize air. A flow of air is directed over a surface that includes a photosensitizer formulation which is activated by light to emit singlet oxygen that inactivates and/or kills pathogens in the air flow. A fan device is employed to generate and direct the flow of air. The fan device includes the photosensitizer formulation disposed on fan blades, rotatable fan shafts, and interior surfaces of a housing. The flow of air is emitted towards an exterior surface. Activation of the photosensitizer by light emits singlet oxygen in the flow of air to inactivate pathogens disposed on the interior surface of the housing and the exterior surface.

14 Claims, 6 Drawing Sheets

(56) References Cited

U.S. PATENT DOCUMENTS 5,344,051 A 9/1994 Brown
5,366,402 A 11/1994 Rudell et al.
5,445,608 A 8/1995 Chen et al.
5,526,957 A 6/1996 Brown et al.
5,534,346 A 7/1996 Robinson
5,569,477 A 10/1996 Nesbitt
5,715,837 A 2/1998 Chen
5,741,316 A 4/1998 Chen et al.
5,766,234 A 6/1998 Chen et al.
5,782,896 A 7/1998 Chen et al.
5,814,008 A 9/1998 Chen et al.
5,827,186 A 10/1998 Chen et al.
5,830,526 A 11/1998 Wilson et al.
5,865,840 A 2/1999 Chen
5,891,062 A 4/1999 Schock et al.
5,997,569 A 12/1999 Chen et al.
6,004,510 A 12/1999 Gilbert et al.
6,080,160 A 6/2000 Chen et al.
6,096,066 A 8/2000 Chen et al.
6,210,425 B1 4/2001 Chen
6,238,426 B1 5/2001 Chen
6,273,904 B1 8/2001 Chen et al.
6,281,611 B1 8/2001 Chen et al.
6,317,691 B1 11/2001 Narayan et al.
6,319,273 B1 11/2001 Chen et al.
6,331,744 B1 12/2001 Chen et al.
6,344,050 B1 2/2002 Chen
6,351,854 B1 3/2002 Whalen et al.
6,416,531 B2 7/2002 Chen
6,420,455 B1 7/2002 Landgrebe et al.
6,443,978 B1 9/2002 Zharov
6,454,789 B1 9/2002 Chen et al.
6,520,669 B1 2/2003 Chen et al.
6,572,839 B2 6/2003 Sugita et al.
6,580,228 B1 6/2003 Chen et al.
6,606,767 B2 8/2003 Wong
6,635,267 B1 10/2003 Miyoshi et al.
6,691,898 B2 2/2004 Hurray
6,692,694 B1 2/2004 Curry et al.
6,846,305 B2 1/2005 Smith et al.
6,860,782 B2 3/2005 Hornsby et al.
7,018,395 B2 3/2006 Chen
7,087,219 B2 8/2006 Burzynski et al.
7,211,056 B2 5/2007 Petelenz et al.
7,288,106 B2 10/2007 Heacock et al.
7,320,158 B2 1/2008 Deto et al.
7,320,786 B2 1/2008 Chen
7,511,031 B2 3/2009 Chen
7,611,033 B2 11/2009 Ganzeboom
7,774,867 B2 8/2010 Orita et al.
7,802,572 B2 9/2010 Hahne
RE42,610 E 8/2011 Schramm
8,057,464 B2 11/2011 Chen et al.
8,226,946 B2 7/2012 Chen
8,283,135 B2 10/2012 Doyle et al.
8,293,802 B2 10/2012 Modak et al.
8,365,316 B2 2/2013 Jan et al.
8,402,568 B2 3/2013 Alstin et al.
8,439,674 B2 5/2013 Li et al.
8,450,359 B2 5/2013 McCoy et al.
8,484,809 B2 7/2013 Fiedler
8,545,120 B2 10/2013 Breidenbach et al.
8,616,414 B2 12/2013 Ciavarniia
8,685,005 B2 4/2014 Dahm et al.
8,685,071 B2 4/2014 Burwell et al.
8,759,092 B2 6/2014 Goodrich
8,956,379 B2 2/2015 Luciano et al.
9,073,066 B2 7/2015 Banks et al.
9,080,976 B2 7/2015 Hackbarth et al.
9,114,971 B2 8/2015 Rasmussen et al.
9,140,030 B2 9/2015 Jin
9,149,651 B2 10/2015 Keltner et al.
9,167,880 B2 10/2015 Wilson et al.
9,278,148 B2 3/2016 Fewkes et al.
9,352,074 B2 5/2016 Gros
9,480,760 B2 11/2016 Appeaning et al.
9,527,918 B2 12/2016 Fiori et al.
9,662,258 B2 5/2017 Slattery, Jr. et al.
9,775,389 B2 10/2017 Azzolin et al.
9,931,656 B2 4/2018 Gonzalez et al.
10,105,386 B2 10/2018 Vehige et al.
10,175,687 B2 1/2019 Lema et al.
10,307,610 B2 6/2019 Keltner et al.
10,327,444 B2 6/2019 Topchik
10,666,928 B2 5/2020 Liu
10,786,592 B2 * 9/2020 Keith .................. B01D 53/885
11,419,543 B1 8/2022 Peyman
11,458,220 B2 10/2022 Chen et al.
11,925,717 B2 3/2024 Chen et al.
12,359,369 B2 7/2025 Chen
2002/0069777 A1 6/2002 Rossini et al.
2002/0088825 A1 7/2002 Laverdure
2003/0035750 A1 2/2003 Neuberger
2003/0114434 A1 6/2003 Chen et al.
2004/0170526 A1 9/2004 Curry et al.
2006/0223729 A1 10/2006 Hamblin et al.
2007/0038204 A1 2/2007 Chen et al.
2007/0059316 A1 3/2007 Pallenberg et al.
2007/0059791 A1 3/2007 Goodrich
2007/0129776 A1 6/2007 Robins et al.
2007/0133935 A1 6/2007 Fine
2007/0142880 A1 6/2007 Barnard et al.
2007/0286878 A1 12/2007 Harruna
2008/0015189 A1 1/2008 Hamblin et al.
2008/0030010 A1 2/2008 Millet Lopez
2008/0051736 A1 * 2/2008 Rioux ....................... A61L 2/08
604/265
2008/0107636 A1 5/2008 Goodrich et al.
2008/0172779 A1 7/2008 Ferguson
2008/0243383 A1 10/2008 Lin
2009/0317293 A1 12/2009 Street et al.
2009/0317436 A1 12/2009 Wilson et al.
2010/0129267 A1 * 5/2010 Akutsu ................... A61L 9/205
422/121
2010/0174223 A1 7/2010 Sakamoto et al.
2010/0241054 A1 9/2010 Dacey, Jr. et al.
2010/0261798 A1 10/2010 Neuss et al.
2010/0274330 A1 10/2010 Burwell et al.
2010/0305436 A1 12/2010 Chen et al.
2010/0313890 A1 * 12/2010 Messier .................... A61L 9/16
128/206.19
2011/0008372 A1 1/2011 Chen
2011/0009464 A1 1/2011 Chen
2011/0014239 A1 1/2011 Goodrich
2011/0093003 A1 4/2011 Lee
2011/0110818 A1 5/2011 Mowbray-D Arbela et al.
2011/0112059 A1 5/2011 Hasan et al.
2011/0152219 A1 6/2011 Stagni et al.
2012/0100039 A1 4/2012 Appeaning et al.
2012/0209359 A1 8/2012 Chen et al.
2013/0060172 A1 3/2013 Palazzolo et al.
2013/0251440 A1 9/2013 Young et al.
2013/0289457 A1 10/2013 Young et al.
2014/0052050 A1 2/2014 Courtin
2014/0076404 A1 3/2014 Tan et al.
2014/0303547 A1 10/2014 Loupis et al.
2015/0202608 A1 * 7/2015 Masaoka ................... A61L 9/01
502/159
2015/0231287 A1 8/2015 Lin et al.
2015/0313608 A1 11/2015 Baudenbacher et al.
2016/0091399 A1 3/2016 Chen et al.
2016/0193338 A1 7/2016 Loupis et al.
2016/0220728 A1 8/2016 Adams et al.
2016/0270472 A1 9/2016 Allen et al.
2016/0270895 A1 9/2016 Zoll et al.
2016/0310758 A1 10/2016 Friedman et al.
2016/0358485 A1 12/2016 Sommer et al.
2017/0056603 A1 3/2017 Cowan et al.
2017/0202279 A1 7/2017 Mazzarolo et al.
2018/0099063 A1 4/2018 Lyons et al.
2018/0160720 A1 6/2018 Von Hasseln
2018/0214552 A1 8/2018 Sui et al.
2018/0243790 A1 8/2018 Grossman et al.
2018/0369560 A1 12/2018 Ball et al.

(56) References Cited

U.S. PATENT DOCUMENTS

| | | | | |
|---|---|---|---|---|
| 2019/0161562 | A1 | 5/2019 | Bakar et al. | |
| 2019/0192719 | A1* | 6/2019 | Drayton | A61L 9/014 |
| 2019/0209857 | A1 | 7/2019 | Brawn et al. | |
| 2019/0314502 | A1 | 10/2019 | Wei et al. | |
| 2020/0289985 | A1* | 9/2020 | Drake | A61L 2/202 |
| 2020/0315280 | A1 | 10/2020 | Kaye | |
| 2021/0346531 | A1 | 11/2021 | Kim et al. | |
| 2022/0054149 | A1 | 2/2022 | Chen et al. | |
| 2022/0054667 | A1 | 2/2022 | Chen et al. | |
| 2022/0054672 | A1 | 2/2022 | Chen et al. | |
| 2022/0061318 | A1 | 3/2022 | Chen et al. | |
| 2022/0062460 | A1 | 3/2022 | Wu et al. | |
| 2022/0062461 | A1 | 3/2022 | Chen et al. | |
| 2022/0143243 | A1* | 5/2022 | Chen | A61L 2/088 |
| 2022/0226530 | A1 | 7/2022 | Suetsugu | |
| 2023/0035662 | A1 | 2/2023 | Chen et al. | |
| 2023/0165988 | A1 | 6/2023 | Chen et al. | |
| 2023/0390430 | A1 | 12/2023 | Chen | |
| 2024/0052560 | A1 | 2/2024 | Chen | |
| 2024/0206737 | A1 | 6/2024 | Buchan et al. | |
| 2025/0041459 | A1 | 2/2025 | Dai et al. | |
| 2025/0073491 | A1 | 3/2025 | Chen | |
| 2025/0082802 | A1* | 3/2025 | Chen | A61L 2/088 |
| 2025/0152987 | A1 | 5/2025 | Chen | |

FOREIGN PATENT DOCUMENTS

| | | | | |
|---|---|---|---|---|
| AU | 2015200474 | B2 | 8/2016 | |
| AU | 2016235788 | A1 | 9/2016 | |
| AU | 2016235771 | B2 | 3/2019 | |
| CA | 2276023 | C | 4/2002 | |
| CA | 2473924 | A1 | 7/2003 | |
| CA | 2537235 | A1 | 1/2005 | |
| CA | 2428099 | C | 1/2009 | |
| CA | 2733752 | C | 1/2014 | |
| CA | 2693491 | C | 10/2014 | |
| CN | 102115951 | B | 7/2012 | |
| CN | 101479438 | B | 5/2014 | |
| CN | 104138310 | A | 11/2014 | |
| CN | 104623702 | A | 5/2015 | |
| CN | 205094776 | U | 3/2016 | |
| CN | 104589717 | B | 3/2017 | |
| CN | 208597758 | U | 3/2019 | |
| CN | 107353723 | B | 5/2020 | |
| CN | 111567937 | A | 8/2020 | |
| EP | 1644082 | A2 | 1/2005 | |
| EP | 1684865 | A1 | 4/2005 | |
| EP | 2181691 | A1 | 5/2010 | |
| EP | 1429993 | B1 | 1/2011 | |
| EP | 1940907 | B1 | 4/2011 | |
| EP | 2428461 | B1 | 4/2013 | |
| GB | 2374856 | A | 10/2002 | |
| GB | 2482745 | A | 2/2012 | |
| JP | 2004-275927 | A | 10/2004 | |
| JP | 2004-350935 | A | 12/2004 | |
| JP | 2005-009065 | A | 1/2005 | |
| JP | 2005-506938 | A | 3/2005 | |
| JP | 2005-112791 | A | 4/2005 | |
| JP | 4238174 | B2 | 3/2009 | |
| JP | 4536377 | B2 | 9/2010 | |
| JP | 2014-004329 | A | 1/2014 | |
| JP | 5632478 | B2 | 11/2014 | |
| JP | 2015-159819 | A | 9/2015 | |
| JP | 2018523517 | A * | 8/2018 | C02F 1/30 |
| KR | 2003-48162 | Y1 | 5/2004 | |
| KR | 10-0822777 | B1 | 4/2008 | |
| KR | 10-2014-0028671 | A | 3/2014 | |
| KR | 10-2017-0076342 | A | 7/2017 | |
| KR | 10-2017-0082259 | A | 7/2017 | |
| KR | 102144502 | B1 | 8/2020 | |
| PL | 230175 | B1 | 9/2018 | |
| RU | 2397127 | C2 | 8/2010 | |
| TW | I610806 | B | 1/2018 | |
| WO | 98/32494 | A1 | 7/1998 | |
| WO | 99/18924 | A1 | 4/1999 | |
| WO | 99/49823 | A1 | 10/1999 | |
| WO | 00/04930 | A2 | 2/2000 | |
| WO | 00/36983 | A1 | 6/2000 | |
| WO | 2004/108249 | A1 | 12/2004 | |
| WO | 2005/004704 | A2 | 1/2005 | |
| WO | 2005/032459 | A2 | 4/2005 | |
| WO | 2005/037372 | A1 | 4/2005 | |
| WO | 2006/086770 | A2 | 8/2006 | |
| WO | 2007/103781 | A2 | 9/2007 | |
| WO | 2008/044222 | A2 | 4/2008 | |
| WO | 2008/046019 | A1 | 4/2008 | |
| WO | 2009/132223 | A1 | 10/2009 | |
| WO | 2010/076658 | A2 | 7/2010 | |
| WO | 2010/151563 | A1 | 12/2010 | |
| WO | 2014/057116 | A1 | 4/2014 | |
| WO | 2014/130740 | A1 | 8/2014 | |
| WO | 2016/039812 | A1 | 3/2016 | |
| WO | 2016/153910 | A1 | 9/2016 | |
| WO | 2018/022926 | A1 | 2/2018 | |
| WO | 2018/151236 | A1 | 8/2018 | |
| WO | 2019/183320 | A1 | 9/2019 | |
| WO | 2021/001441 | A1 | 1/2021 | |
| WO | 2021/001445 | A1 | 1/2021 | |
| WO | 2022/103775 | A1 | 5/2022 | |

OTHER PUBLICATIONS

Quoc et al., "Optimization of an Accelerometer and Gyroscope-Based Fall Detection Algorithm," Journal of Sensors, Apr. 2015, vol. 2015, Article ID 452078, pp. 1-8.

Hwang et al., "Study of Singlet Oxygen Dynamics on Silicon Polymer Matrix," Journal of Analytical Methods in Chemistry, 2019, vol. 2019, pp. 1-6.

Ismail et al., "Efficacy of a Novel Light-Activated Antimicrobial Coating for Disinfecting Hospital Surfaces," Infection Control and Hospital Epidemiology, 2011, vol. 32, No. 11, pp. 1130-1132.

Ji et al., "In Vivo Measurements of Human Brain Displacement," Stapp Car Crash Journal, Nov. 2004, vol. 48, pp. 1-11.

Jaesung et al., "Photosensitized Production of Singlet Oxygen via C60 Fullerene Covalently Attached to Functionalized Silica-coated Stainless-Steel Mesh: Remote Bacterial and Viral Inactivation," Applied Catalysts B: Environmental, 2020, vol. 270, Article No. 118862, pp. 1-9.

Michele et al., "Light Sources and Dosimetry Techniques for Photodynamic Therapy," Photochemistry and Photobiology, 2020, vol. 96, pp. 280-294.

Kim, Sungho, "High-Speed Incoming Infrared Target Detection by Fusion of Spatial and Temporal Detectors," Sensors, Mar. 2015, vol. 15, No. 4, pp. 7267-7293.

Kino et al., "Commentary on the Phototoxicity and Absorption of Vitamin B2 and Its Degradation Product, umichrome," Pharmaceutica Analytica Acta, 2015, vol. 6, Iss. 8, pp. 1-3.

Kitchen Theory, "Lecithin & Culinary Foam," https://kitchen-theory.com/culinary-foam/, Accessed: Nov. 15, 2021, pp. 1-4.

Klasse, P.J., "Molecular determinants of the ratio of inert to infectious virus particles," Progress in Molecular Biology and Translational Science, 2015, vol. 129, pp. 285-326.

Klausberger et al., "One-shot vaccination with an insect cell-derived low-dose influenza A H7 virus-like particle preparation protects mice against H7N9 challenge," Vaccine, 2014, vol. 32, Iss. 3, pp. 355-362.

Komaiko et al., "Formation of Food-Grade Nanoemulsions Using Low-Energy Preparation Methods: A Review of Available Methods," Comprehensive Reviews in Food Science and Food Safety, 2016, vol. 15, pp. 331-352.

Koral et al., "Alterations in cerebrospinal fluid flow dynamics and pressure gradient generated by acute and chronic changes in intraabdominal pressure: Early results of MRI measurements performed on volunteers at 3 Tesla," European Society of Radiology, EPOS, 2010, Poster No. C-2474, pp. 1-10.

Kumar et al., "Sensing Molecules with Metal-Organic Framework Functionalized Graphene Transistors," Advanced Materials, 2021, vol. 33, Article No. 2103316, pp. 1-12.

(56) References Cited

OTHER PUBLICATIONS

Lee et al., "Aerosol Particle Size Distribution and Genetic Characteristics of Aerosolized Influenza A H1N1 Virus Vaccine Particles," Aerosol and Air Quality Research, 2011, vol. 11, pp. 230-237.
Lee et al., "The photodynamic therapy on *Streptococcus mutans* biofilms using erythrosine and dental halogen curing unit," International Journal of Oral Science, 2012, vol. 4, pp. 196-201.
LFA Tablet Presses, "Tablet Binders," https://www.lfatabletpresses.com/articles/tablet-binders, Accessed: Dec. 6, 2021, pp. 1-8.
Li, Dao et al., "Brain Injury Differences in Frontal Impact Crash Using Different Simulation Strategies," Computational and Mathematical Methods in Medicine, 2015, vol. 2015, Article ID 348947, pp. 1-8.
Ji-Yuan et al., "Blue light induced free radicals from riboflavin on *E. coli* DNA damage," Journal of Photochemistry and Photobiology B: Biology, Feb. 2013, vol. 119, pp. 60-64.
Instructables Living, "Bubble Machine," https://www.instructables.com/Bubble-Machine/, Accessed: Nov. 30, 2021, pp. 1-6.
MacoPharma, "THERAFLEX-MB Plasma," https://www.mhlw.go.jp/shingi/2008/05/dl/s0523-7j.pdf, Accessed: Dec. 1, 2021, pp. 1-33.
Makdoumi et al., "Different photodynamic effects of blue light with and without riboflavin on methicillin-resistant *Staphylococcus aureus* (MRSA) and human keratinocytes in vitro," Lasers in Medical Science, 2019, vol. 34, No. 9, pp. 1799-1805.
Malewar, Amit, "Tengujo, the world's thinnest paper, almost completely transparent," Inceptive Mind, https://www.inceptivemind.com/tengujo-worlds-thinnest-paper-nearly-transparent/13273/, Accessed: Nov. 15, 2021, pp. 1-5.
Marcus et al., "In Vitro Analysis of Virus Particle Subpopulations in Candidate Live-Attenuated Influenza Vaccines Distinguishes Effective from ineffective Vaccines," Journal of Virology, 2010, vol. 84, No. 21, pp. 10974-10981.
Martin, GT, "Acute brain trauma," Annals of the Royal College of Surgeons of England, Jan. 2016, vol. 98, No. 1, pp. 6-10.
Matsui et al., "Real-Time Near-Infrared Fluorescence-Guided Identification of the Ureters using Methylene Blue," Surgery, 2010, vol. 148, No. 1, pp. 78-86.
Maves et al., "Immunogenicity of a Psoralen-Inactivated Dengue Virus Type 1 Vaccine Candidate in Mice," Clinical and Vaccine Immunology, 2010, vol. 17, No. 2, pp. 304-306.
Meller et al., "Photodisinfection Therapy: Essential Technology for Infection Control," The Infection Prevention Strategy, Jan. 2020, https://infectioncontrol.tips/2020/01/17/photodisinfection-therapy/, Accessed: Jun. 7, 2022, pp. 1-13.
Federica et al., "In vitro photo-induced cytotoxic activity of *Citrus bergamia* and *C. medica* L. cv. *diamante* peel essential oils and identified active coumarins," Pharmaceutical Biology, vol. 48, No. 9, pp. 1059-1065.
Mertes et al., "Methylene blue-treated plasma: An increased allergy risk?," The Journal of Allergy and Clinical Immunology, Letters to the Editor, 2012, vol. 130, Iss. 3, pp. 808-812.
Mesquita et al., "Revisiting Current Photoactive Materials for Antimicrobial Photodynamic Therapy," Molecules, 2018, vol. 23, No. 2424, pp. 1-47.
Gabriele et al., "Environmental Contaminants in Hospital Settings and Progress in Disinfecting Techniques," BioMed Research International, 2013, vol. 2013, pp. 1-8.
Meurice et al., "Immunogenicity and Safety of a Live Attenuated Varicella Vaccine (Oka/SB Bio) in Healthy Children," The Journal of Infectious Diseases, 1996, vol. 174, Supplement 3, Pages S324-S329.
Meyer et al., "Aerosolized Ebola vaccine protects primates and elicits lung-resident T cell responses," The Journal of Clinical Investigation, 2015, vol. 125, No. 8, pp. 3241-3255.
Midden et al., "Singlet Oxygen Generation for Solution Kinetics: Clean and Simple," Journal of the American Chemical Society, Jun. 1983, vol. 105, No. 13, pp. 4129-4135.
Mills et al., "Ultraviolet germicidal irradiation of influenza-contaminated N95 filtering facepiece respirators," American Journal of Infection Control, 2018, vol. 46, Iss. 7, pp. e49-e55.
Molitch-Hou, Michael, "First 3D Printed Fiber Optics Created by University of Sydney Researchers with Desktop BD Printer," 3D Printing Industry, https://3dprintingindustry.com/news/first-3d-printed-fiber-optics-createdby-university-bf-sydney-researchers-with-desktop-3d-printer-55047/, 2015, Accessed: Jun. 30, 2021, p. 1.
Moller-Breitkreutz et al., "Inactivation of viruses by chemically and photochemically generated singlet molecular oxygen," Journal of Photochemistry & Photobiology B: Biology, 1995, vol. 30, Iss. 1, pp. 63-70.
Monath et al., "A live, attenuated recombinant West Nile virus vaccine," Proceedings of the National Academy of Sciences, 2006, vol. 103, No. 17, pp. 6694-6699.
Moses, Allistair et al., "Radar-Based Detection and Identification for Miniature Air Vehicles," IEEE International Conference on Control Applications (CCA), Sep. 2011, pp. 933-940.
Myer et al., "Analysis of head impact exposure and brain microstructure response in a season-long application of a jugular vein compression collar: a prospective, neuroimaging investigation in American football," British Journal of Sports Medicine, Oct. 2016, vol. 50, No. 20, pp. 1-11.
Naito et al., "Single-molecule detection of airborne singlet oxygen," Journal of the American Chemical Society, 2006, vol. 128, No. 51, pp. 16430-16431.
Nakonechny et al., "Aspects of Photodynamic Inactivation of Bacteria," Microorganisms, 2020, Chapter 7, pp. 131-151.
Navarro et al., "A Machine Learning Approach to Pedestrian Detection for Autonomous Vehicles Using High-Definition 3D Range Data," Sensors, 2017, vol. 17, No. 1:18, pp. 1-20.
Ng et al., "A Mechanistic End-to-End Concussion Model That Translates Head Kinematics to Neurologic Injury," Frontiers in Neurology, Jun. 2017, vol. 8, Article 269, pp. 1-18.
Noimark et al., "Incorporation of methylene blue and nanogold into polyvinyl chloride catheters; A new approach for light-activated disinfection of surfaces," Journal of Materials Chemistry, 2012, vol. 22, Iss. 30, pp. 15388-15396.
Noimark et al., "Light-activated antimicrobial surfaces with enhanced efficacy induced by a dark-activated mechanism," Chemical science, 2014, vol. 5, pp. 2216-2223.
Ogilby, Peter R., "Singlet oxygen: There is indeed something new under the sun," Chemical Society Reviews, 2010, vol. 39, No. 8, pp. 3181-3209.
Omnexus: The material selection platform, "Clear Polypropylene (PP) for Transparent Polymer Applications," https://omnexus.specialchem.com/centers/clear-polypropylene/, Accessed: Jul. 1, 2021, p. 1.
Office Communication for U.S. Appl. No. 17/958,639 mailed Nov. 8, 2023, 10 Pages.
Office Communication for U.S. Appl. No. 18/205,082 mailed Nov. 8, 2023, 14 Pages.
"What is Photodisinfection?," Ondine Biomedical Inc., https://ondinebio.com/technology/, Accessed: Jun. 7, 2022, pp. 1-4.
Adepu et al., "Controlled Drug Delivery Systems: Current Status and Future Directions, " Molecules, Sep. 2021, vol. 26, No. 19, Article No. 5905, pp. 1-45.
Aebisher et al., "Superhydrophobic Surfaces as a Source of Airborne Singlet Oxygen through Free Space for Photodynamic Therapy," ACS Applied Bio Materials, 2020, vol. 3, No. 4, pp. 2370-2377.
Akasov et al., "Photodynamic therapy of melanoma by blue-light photoactivation of flavin mononucleotide," Scientific Reports, 2019, vol. 9, Article No. 9679, pp. 1-11.
Alander et al., "A Review of Indocyanine Green Fluorescent Imaging in Surgery," international Journal of Biomedical Imaging, 2012, vol. 2012, pp. 1-26.
Almeida et al., "Phage Therapy and Photodynamic Therapy: Low Environmental Impact Approaches to Inactivate Microorganisms in Fish Farming Plants," Marine Drugs, 2009, vol. 7, No. 3, pp. 268-313.
Alven et al., "Hyaluronic Acid-Based Scaffolds as Potential Bioactive Wound Dressings," Polymers, 2021, vol. 13, No. 2102, pp. 1-20.

(56) References Cited

OTHER PUBLICATIONS

Babbs, Charles F., "Brain motion and deformation during closed head injury in the presence of cerebrospinal fluid," Weldon School of Biomedical Engineering Faculty Publications, Jun. 2004, Paper 41, pp. 1-39.
Gladimir et al., "On the Light Penetration in Natural Sands," 2019 IEEE International Geoscience and Remote Sensing Symposium (IGARSS 2019), 2019, pp. 6933-6936.
Barrett et al., "Vero cell technology for rapid development of inactivated whole virus vaccines for emerging viral diseases," Expert Review of Vaccines, 2017, vol. 16, Iss. 9, pp. 883-894.
Dorota et al., "Bacterial Inactivation by a Singlet Oxygen Bubbler: Identifying Factors Controlling the Toxicity of 102 Bubbles," Environmental Science & Technology, 2012, vol. 46, No. 21, pp. 12098-12104.
Bayly et al., "Deformation of the human brain induced by mild acceleration," Journal of Neurotrauma, NIH Public Access, Author Manuscript, 2005, PMCID PMC2377024, pp. 1-18.
Bazaz et al., "3D Printing of Inertial Microfluidic Devices," Scientific Reports, 2020, vol. 10, Article No. 5929, pp. 1-14.
Bhat et al., "Effectiveness of erythrosine-mediated photodynamic antimicrobial chemotherapy on dental plaque aerobic microorganisms: A randomized controlled trial," Journal of Indian Society of Periodontology, 2017, vol. 21, Iss. 3, pp. 210-215.
Bonetta et al., "Photocatalytic bacterial inactivation by TiO2-coated surfaces," AMB Express, 2013, vol. 3, Article 59, pp. 1-8.
Borkar et al., "Techniques Employed in Production of Traditional Vaccines Commonly Used by Military Forces: A Review," Journal of Archives in Military Medicine, 2019, vol. 7, No. 1-2, pp. 1-12.
Boyce, John M., "Modern technologies for improving cleaning and disinfection of environmental surfaces in hospitals," Antimicrobial Resistance and Infection Control, 2016, vol. 5, Article 10, pp. 1-10.
Buettner et al., "Hydrogen Peroxide and Hydroxyl Radical Formation by Methylene Blue in the Presence of Ascorbic Acid," Radiation and Environmental Biophysics, 1984, vol. 23, pp. 235-243.
Bull et al., "Transmissible Viral Vaccines," Trends in Microbiology, 2018, vol. 26, No. 1, pp. 6-15.
Cagno et al., "Methylene Blue has a potent antiviral activity against SARS-COV-2 and H1N1 influenza virus in the absence of UV-activation in vitro," Scientific Reports, Jul. 2021, vol. 11, Article No. 14295, pp. 1-8.
Fernando et al., "Obstacle Recognition Based on Machine Learning for On-Chip LiDAR Sensors in a Cyber-Physical System," Sensors, Sep. 2017, vol. 17, No. 9:2109, pp. 1-14.
CDC—The National institute for Occupational Safety and Health (NIOSH), https://www.cdc.gov/niosh/index.htm, Accessed: Nov. 15, 2021, p. 1.
Chemistry Industry, "Emulsifiers," https://www.chemistryindustry.biz/emulsifiers.html, Accessed: Nov. 15, 2021, pp. 1-9.
Citerio et al., "Induced abdominal compartment syndrome increases intracranial pressure in neurotrauma patients: A prospective study," Critical Care Medicine, Jul. 2001, vol. 29, No. 7, pp. 1466-1471.
Cytiva, "Influenza vaccine manufacturing," https://www.cytivalifesciences.com/en/us/solutions/bioprocessing/ knowledge-center/influenza-vaccine-manufacturing/, Accessed: Jun. 30, 2021, pp. 1-10.
Dancer, Stephanie J., "Controlling Hospital-Acquired Infection: Focus on the Role of the Environment and New Technologies for Decontamination," Clinical Microbiology Reviews, 2014, vol. 27, No. 4, pp. 665-690.
De Ponte Muller, Fabian, "Survey on Ranging Sensors and Cooperative Techniques for Relative Positioning of Vehicles," Sensors, Jan. 2017, vol. 17, No. 2:271, pp. 1-27.
Dias et al., "COVID-19: Beyond the virus. The use of photodynamic therapy for the treatment of infections in the respiratory tract," Photodiagnosis and Photodynamic Therapy, Letter to the Editor, 2020, vol. 31, pp. 1-2.
Divangahi et al., "Trained immunity, tolerance, priming and differentiation: distinct immunological processes," Nature Immunology, 2021, vol. 22, pp. 2-6.
Eickmann et al., "Inactivation of Ebola virus and Middle East respiratory syndrome coronavirus in platelet concentrates and plasma by ultraviolet C light and methylene blue plus visible light, respectively," Transfusion, 2018, vol. 58, pp. 2202-2207.
Evonik, "A Broad Range of Standard, Custom and Specialized Biodegradable Polymers for Medical Applications," https://healthcare.evonik.com/en/medical-devices/biodegradable-materials/resomer-portfolio, Accessed: Nov. 22, 2021, pp. 1-3.
Fecht, Sara, "The First Fully 3-D Printed LEDs Are Here," https://www.popsci.com/article/technology/first-fully-3-d-printed-leds-are-here/, 2014, Accessed: Jun. 30, 2021, pp. 1-4.
Felgentrager et al., "Singlet oxygen generation in porphyrin-doped polymeric surface coating enables antimicrobial effects on *Staphylococcus aureus*," Physical Chemistry Chemical Physics: PCCP, 2014, vol. 16, No. 38, pp. 20598-20607.
Feng et al., "Relative brain displacement and deformation during constrained mild frontal head impact," Journal of the Royal Society Interface, May 2010, vol. 7, pp. 1677-1688.
Fernandez et al., "Singlet oxygen generation by photodynarnic agents," Journal of Photochemistry & Photobiology B: Biology, 1997, vol. 37, pp. 131-140.
Fracalossi et al., "Singlet oxygen production by combining erythrosine and halogen light for photodynamic Inactivation of *Streptococcus mutans*," Photodiagnosis and Photodynamic Therapy, 2016, vol. 15, pp. 127-132.
Gabay, Jon, "Sensor-Based Collision Avoidance Solutions for Drone Fleets," DigiKey, https://www.digikey.com/en/articles/sensor-based-collision avoidance-solutions-for-drone-fleets, Mar. 2016, Accessed: Jun. 6, 2023, pp. 1-6.
Gahleitner et al., "Sterilization effects on polypropylene: Technology and polymer type effects, " TAPPI European PLACE Conference, 2003, pp. 1-7.
Gao et al., "Nano-photosensitizer based on layered double hydroxide and isophthalic acid for singlet oxygenation and photodynamic therapy," Nature Communications, 2018, vol. 9, No. 1, pp. 1-10.
Geeraedts et al., "Superior Immunogenicity of Inactivated Whole Virus H5N1 Influenza Vaccine is Primarily Controlled by Toll-like Receptor Signalling," PLoS Pathogens, 2008, vol. 4, Iss. 8, pp. 1-8.
Gonzalez, Murielle, "Hartalega: Expansion plan on track," Cleanroom Technology, 2019, https://cleanroomtechnology.com/news/article_page/Hartalega_Expansion_plan_on_track/153507, Accessed: Apr. 6, 2022, pp. 1-4.
Hankaniemi et al., "A comparative study of the effect of UV and formalin inactivation on the stability and immunogenicity of a Coxsackievrius B1 vaccine," Vaccine, 2019, vol. 37, Iss. 40, pp. 5962-5971.
Keisuke et al., "Curved acceleration path of ultrasound-driven air flow," Journal of Applied Physics, vol. 125, Article No. 054902, pp. 1-6.
Hasenleitner et al., "In the Right Light: Photodynamic Inactivation of Microorganisms Using a LED-Based Illumination Device Tailored for the Antimicrobial Application," Antibiotics, Dec. 2019, vol. 9, pp. 1-13.
Henneberry, Brittany, "How Surgical Masks are Made," Thomas Publishing Company, https://www.thomasnet.com/articles/other/how-surgical-masks-are-made/, Accessed: Jul. 1, 2021, pp. 1-6.
Hidakawashi Co., Ltd., "Japanese Paper TENGU," https://www.hidakawashi.com/paper-TENGU/index.html, Accessed: Nov. 15, 2021, pp. 1-2.
Hillary et al., "Use of methylene blue and near-infrared fluorescence in thyroid and parathyroid surgery," Langenbeck's Archives of Surgery, 2018, vol. 403, pp. 111-118.
Hiscox et al., "Magnetic resonance elastography (MRE) of the human brain: technique, findings and clinical applications," Physics in Medicine & Biology, Nov. 2016, vol. 61, pp. R401-R437.
Hogan, Quinn H. et al., "Magnetic Resonance Imaging of Cerebrospinal Fluid vol. and the Influence of Body Habitus and Abdominal Pressure," Anesthesiology, Jun. 1996, vol. 84, No. 6, pp. 1341-1349.
Holliday et al., "Concussion: A National Challenge," The Bridge, National Academy of Engineering, 2016, vol. 46, No. 1, pp. 1-132.
Office Communication for U.S. Appl. No. 17/522,811 mailed Apr. 14, 2022, 7 Pages.

(56) References Cited

OTHER PUBLICATIONS

Office Communication for U.S. Appl. No. 17/522,811 mailed Jan. 27, 2022, 10 Pages.
Office Communication for U.S. Appl. No. 17/958,639 mailed Aug. 8, 2023, 9 Pages.
Office Communication for U.S. Appl. No. 17/958,639 mailed Apr. 25, 2023, 10 Pages.
Office Communication for U.S. Appl. No. 17/958,639 mailed Jan. 6, 2023, 6 Pages.
Office Communication for U.S. Appl. No. 18/100,993 mailed Jun. 15, 2023, 11 Pages.
Office Communication for U.S. Appl. No. 18/100,993 mailed Oct. 11, 2023, 12 Pages.
Office Communication for U.S. Appl. No. 18/100,993 mailed Apr. 13, 2023, 6 Pages.
Office Communication for U.S. Appl. No. 18/100,993 mailed Dec. 21, 2023, 4 Pages.
Office Communication for U.S. Appl. No. 18/231,922 mailed Dec. 29, 2023, 8 Pages.
Piccirillo et al., "Antimicrobial activity of methylene blue and toluidine blue O covalently bound to a modified silicone polymer surface," Journal of Materials Chemistry, 2009, vol. 19, Iss. 34, pp. 6167-6171.
Plotino et al., "Photodynamic therapy in endodontics," International Endodontic Journal, Jun. 2019, vol. 52, Issue 6, pp. 760-774.
Post et al., "Pediatric concussion: biomechanical differences between outcomes of transient and persistent(> 4 weeks) postconcussion symptoms," Journal of Neurosurgery: Pediatrics, Jun. 2017, vol. 19, No. 6, pp. 641-651.
Prausnitz et al., "Microneedle-based vaccines," Vaccines for Pandemic Influenza, Current Topics in Microbiology and Immunology, 2009, vol. 333, pp. 369-393.
Pushalkar et al., "Superhydrophobic Photosensitizers: Airborne 102 Killing of an in Vitro Oral Biofilm at the Plastron Interface," ACS Applied Materials & Interfaces, 2018, vol. 10, No. 30, pp. 25819-25829.
Pyrek, Kelly M., "Portable Medical Equipment: A Significant Source of Transmission," Infection Control Today, https://www.infectioncontroltoday.com/view/portable-medical-equipment-significant-source-transmission/, Accessed: Jul. 2, 2021, pp. 1-9.
Quan et al., "Dose sparing enabled by skin immunization with influenza virus-like particle vaccine using microneedles," Journal of Controlled Release, 2010, vol. 147, Iss. 3, pp. 326-332.
Radiology Info, "Intravascular Ultrasound," https://www.radiologyinfo.org/en/info/ultrasound-intravascular, Accessed: Nov. 22, 2021, pp. 1-6.
Rajesh, S. et al., "Antimicrobial photodynamic therapy: An overview," Journal of Indian Society of Periodontology, 2011, vol. 15, Iss. 4, pp. 323-327.
Russotto, Vincenzo et al., "Bacterial contamination of inanimate surfaces and equipment in the intensive care unit," Journal of Intensive Care, 2015, vol. 3, Article 54, pp. 1-8.
Jerard et al., "Main Properties of the THERAFLEX MB-Plasma System for Pathogen Reduction," Transfusion Medicine and Hemotherapy, 2011, vol. 38, No. 1, pp. 55-64.
Shang et al., "Accelerated In Vitro Degradation of Optically Clear Low 13-Sheet Silk Films by Enzyme-Mediated Pretreatment," Translational Vision Science & Technology, vol. 2, No. 3, Article 2, pp. 1-11.
Sharma et al., "Natural Edible Oils: Comparative Health Aspects of Sesame, Coconut, Mustard (Rape Seed) and Groundnut (Peanut) A Biomedical Approach," Biomedical Journal of Scientific & Technical Research, 2017, vol. 1, Iss. 5, pp. 1375-1377.
Chikara et al., "Near-infrared photothernal/photodynamic therapy with indocyanine green induces apoptosis of hepatocellular carcinoma cells through oxidative stress," Scientific Reports, vol. 7, Article No. 13958, pp. 1-8.
Sigma-Aldrich, "Hyaluronic acid sodium salt" https//www.sigmaaldrich.com/US/en/procluc1/sigma/h5542, Accessed: Nov. 22, 2021, pp. 1-5.
Siracusa, Valentina, "Food Packaging Permeability Behaviour: A Report," International Journal of Polymer Science, 2012, vol. 2012, pp. 1-11.
Slobounov, Semyon M. et al., "The effect of repetitive subconcussive collisions on brain integrity in collegiate football players over a single football season: A multi-modal neuroimaging study," NeuroImage: Clinical, 2017, vol. 14, pp. 708-718.
Smartblend, "Cocktail foams, airs and bubbles—How to make them," https://www.smartblend.co.uk/blog/cocktail-foams-airs-and-bubbles-and-how-to-make-them, Accessed: Dec. 6, 2021, pp. 1-16.
Spagnul et al., "Immobilized Photosensitisers for antimicrobial applications," Journal of Photochemistry and Photobiology, 2015, vol. 150, pp. 11-30.
Sunday et al., "A simple, inexpensive method for gas-phase singlet oxygen generation from sensitizer-impregnated filters: Potential application to bacteria/virus inactivation and pollutant degradation," Science of the Total Environment, 2020, vol. 746, Article No. 141186, pp. 1-6.
Tamstech, "Air Permeable (Breathable) Film," http://tamstech.net/airfilm/, Accessed: Jul. 2, 2021, pp. 1-6.
Trempolec et al., "Photodynamic Therapy-Based Dendritic Cell Vaccination Suited to Treat Peritoneal Mesothelioma," Cancers, Feb. 2020, vol. 12, pp. 1-16.
University of Southampton, "New Optical Fiber 3D Printing Technique," Optik & Photonik, 2015, vol. 10, Iss. 4, p. 17.
Ursa BioScience, "Singlet Oxygen Sensitizers," https://ursabioscience.com/technology/singlet-oxygen-sensitizer, Accessed: Mar. 2, 2021, pp. 1-6.
Verma et al., "Visualizing the effectiveness of face masks in obstructing respiratory jets," Physics of Fluids, 2020, vol. 32, pp. 1-7.
Victoria et al., "Viral Nucleic Acids in Live-Attenuated Vaccines: Detection of Minority Variants and an Adventitious Virus," Journal of Virology, 2010, vol. 84, No. 12, pp. 6033-6040.
Waheed et al., "3D printed microfluidic devices: enablers and barriers," The Royal Society of Chemistry, Lab Chip, 2016, vol. 16, Iss. 11, pp. 1-21.
Wakayama et al., "Magnetic Acceleration of Inllaled and Exhaled Flows in Breathing," Japanese Journal of Applied Physics, 2000, vol. 39, pp. L262-L264.
Waldman et al., "Immunization Against influenza Prevention of illness in Man by Aerosolized Inactivated Vaccine," JAMA, 1969, vol. 207, No. 3, pp. 520-524.
Wang et al., "Choosing optimal wavelength for photodynamic therapy of port wine stains by mathematic simulation," Journal of Biomedical Optics, 2011, vol. 16, No. 9, pp. 1-9.
Weaver, Eric A., "Dose Effects of Recombinant Adenovirus Immunization in Rodents," Vaccines, 2019, vol. 7, No. 4:144, pp. 1-11.
Wojnarowicz et al., "Considerations for Experimental Animal Models of Concussion, Traumatic Brain Injury, and Chronic Traumatic Encephalopathy—These Matters Matter," Frontiers in Neurology, Jun. 2017, vol. 8, Article 240, pp. 1-14.
Wood et al., "Erythrosine is a potential photosensitizer for the photodynamic therapy of oral plaque biofilms," Journal of Antimicrobial Chemotherapy, 2006, vol. 57, Iss. 4, pp. 680-684.
Woolley et al., "Light Penetration and Light-induced Seed Germination in Soil," Plant Physiology, Apr. 1978, vol. 61, No. 4, pp. 597-600.
Wu et al., "A Compact Magnetic Field-Based Obstacle Detection and Avoidance System for Miniature Spherical Robots," Sensors, May 2017, vol. 17, No. 6:1231, pp. 1-20.
Yamada, Shinya, "Cerebrospinal fluid physiology: visualization of cerebrospinal fluid dynamics using the magnetic resonance imaging Time-Spatial Inversion Pulse method," Croatian Medical Journal, Aug. 2014, vol. 55, No. 4, pp. 337-346.
Yang et al., "3D Printing of Polymeric Multi-Layer Micro-Perforated Panels for Tunable Wideband Sound Absorption," Polymers, 2020, vol. 12, No. 360, pp. 1-17.
Jing et al., "Green preparation of carbon dots by Jinhua bergamot for sensitive and selective fluorescent detection of Hg2+ and Fe3+," Sensors and Actuators B: Chemical, 2015, vol. 214, pp. 29-35.

(56) References Cited

OTHER PUBLICATIONS

Zhao et al., "Singlet oxygen generation on porous superhydrophobic surfaces: effect of gas flow and sensitizer wetting on trapping efficiency," The Journal of Physical Chemistry A, 2014, vol. 118, No. 45, pp. 10364-10371.
Zhu et al., "In Vivo Measurements of Human Brain Displacement," 2003 Summer Bioengineering Conference, Jun. 2003, pp. 1-2.
International Preliminary Report on Patentability Chapter I for International Patent Application No. PCT/JS2021/058678 mailed May 25, 2023, 6 Pages.
International Preliminary Report on Patentability Chapter I for International Patent Application No. PCT/JS2021/046722 mailed Mar. 2, 2023, 7 Pages.
International Search Report and Written Opinion for International Patent Application No. PCT/US2021/058678 mailed Jan. 25, 2022, 8 Pages.
International Search Report and Written Opinion for International Patent Application No. PCT/US2021/046416 mailed Nov. 8, 2021, 9 Pages.
International Search Report and Written Opinion for International Patent Application No. PCT/US2021/046417 mailed Nov. 30, 2021, 11 Pages.
International Search Report and Written Opinion for International Patent Application No. PCT/US2021/046419 mailed Feb. 2, 2022, 11 Pages.
International Search Report and Written Opinion for International Patent Application No. PCT/US2021/046722 mailed Dec. 6, 2021, 9 Pages.
International Search Report and Written Opinion for International Patent Application No. PCT/US2021/048444 mailed Feb. 1, 2022, 14 Pages.
Office Communication for U.S. Appl. No. 17/522,811 mailed Jul. 26, 2022, 9 Pages.
Office Communication for U.S. Appl. No. 18/205,082 mailed Aug. 16, 2023, 13 Pages.
Office Communication for U.S. Appl. No. 18/231,922 mailed Mar. 28, 2024, 12 Pages.
Office Communication for U.S. Appl. No. 18/205,082 mailed May 16, 2024, 15 Pages.
Kim et al., "Photocatalytic detoxification of a sulfur mustard simulant under realistic conditions by imidazoline-based porous organic polymer composites", Cell Reports Physical Science, vol. 3, Issue 5, 100888, May 18, 2022, pp. 1-19.
Ayoub et al., "Air oxidation of sulfur mustard gas simulants using a pyrene-based metal-organic framework photocatalyst", Beilstein Journal of Nanotechnology, vol. 10, 2019, pp. 2422-2427.
Ayoub et al., "Air oxidation of sulfur mustard gas simulants using a pyrene-based metal-organic framework photocatalyst", Supporting Information, Beilstein Journal of Nanotechnology, vol. 10, 2019, pp. S1-S10.
Atilgan et al., "Detoxification of a Sulfur Mustard Simulant Using a BODIPY Functionalized Zirconium-Based Metal-Organic Framework", ACS Appl. Mater. Interfaces 2017, vol. 9, pp. 24555-24560.
Atilgan et al., "Detoxification of a Sulfur Mustard Simulant Using a BODIPY Functionalized Zirconium-Based Metal-Organic Framework", Supporting Information, ACS Appl. Mater. Interfaces 2017, vol. 9, pp. S1-S14.
Office Communication for U.S. Appl. No. 18/205,082 mailed Jan. 28, 2025, 16 Pages.
Office Communication for U.S. Appl. No. 18/231,922 mailed Feb. 10, 2025, 12 Pages.
Office Communication for U.S. Appl. No. 18/205,082 mailed Jul. 31, 2025, 17 Pages.
Office Communication for U.S. Appl. No. 18/205,082 mailed Apr. 7, 2025, 4 Pages.
Office Communication for U.S. Appl. No. 18/231,922 mailed Apr. 9, 2025, 4 Pages.
Office Communication for U.S. Appl. No. 18/205,082 mailed Apr. 22, 2025, 17 Pages.
Office Communication for U.S. Appl. No. 18/231,922 mailed May 9, 2025, 9 Pages.
Office Communication for U.S. Appl. No. 18/394,020 mailed Apr. 7, 2026, 30 Pages.
Office Communication for U.S. Appl. No. 18/599,518 mailed Apr. 6, 2026, 18 Pages.

* cited by examiner

AIR SANITIZATION

CROSS-REFERENCES TO RELATED APPLICATIONS

This application is a Utility patent application based on previously filed U.S. Provisional Patent Application No. 63/415,902, filed on Oct. 13, 2022, the benefit of the filing date of which is hereby claimed under 35 U.S.C. § 119(e) and the contents of which is herein incorporated by reference in its entirety.

BACKGROUND

Air purification devices and equipment are important for health maintenance especially when pathogens contaminate the air such as has, and is occurring as a result of the SARS-CoV2-2 outbreak. Other respiratory pathogens such as influenza, respiratory syncytial virus, measles, monkeypox, rhinoviruses, mumps, hantavirus, and other pathogens can be transmitted through the air especially during outbreaks, along with chemical and biological agents deliberately or accidentally released as part of bioterror events or laboratory accidents.

Mitigations measures such as ultraviolet light or ozone emitting devices have downsides including tissue toxicity risks. Air filters that are of high filtration capability such as HEPA filters can require powerful noisy fans to push air though dense materials, and as such can be large, bulky devices if used for large volume spaces such as rooms. Filters and other devices such as electrostatic precipitators may only trap airborne pathogens, and do not inactivate or actively kill the pathogens. Clearly, there is a need for improved air purification that actively inactivates and/or kill pathogens in the air, without the toxicity risks to the eyes and skin that can be caused by ultraviolet light, or lung, eye and other toxicity risks caused by ozone production.

SUMMARY

The features for one or more embodiments may include one or more of the following limitations:

- A tangential fan design that creates a curtain of disinfected air that can be directed anterior to the face of a user of the device;
- Fan blades comprised of a material such as synthetic or natural fibers that easily and readily accept at least one photosensitizer and other substances;
- A miniature rechargeable electric motor which enable rotation of the shaft that the fan blades are attached to;
- A shaft which is comprised of a polymer or a metal, which is stiff or flexible, enabling the tangential fan device to be configured into a curved shape if desired;
- Fan blades that are optionally flexible, or that incorporate stiffening struts;
- Variable speed electric motor that can rotate the fan blades slower or faster;
- Fan blade configuration that is flat, curved, or in a screw shape;
- External housing for the fan shaft/blade assembly that incorporates at least one photosensitizer;
- A light source which may be ambient light, or an incorporated light source such as at least one light emitting diode, or which may also incorporate non-imaging lenses to direct light onto the fan blades and the interior of the housing incorporating at least one photosensitizer;

- Fan blade number can range from two opposing blades to 20 blades spaced apart uniformly;
- Fan blade rotation speed can vary from 10 to 100,000 revolutions per minute;
- Fan blade dimensions can range from 1.0 cm to 500.0 cm in length and 1.0 cm to 10.0 cm in width;
- Fan blade and housing optionally incorporate phase change materials for heating and cooling of expelled air;
- A reservoir which is refillable or exchangeable contains at least one photosensitizer formulation, is used to recharge the fan blade(s) and inner surface of the fan housing;
- The cylindrical housing coated with at least one photosensitizer can also rotate around an axis;
- An ultrasonic motor can be utilized to spin the fan blades; and/or
- Techniques of incorporating at least one photosensitizer into a fabric or surface.

VARIOUS EMBODIMENTS

In one or more embodiments, the tangential fan housing is lined with natural and/or synthetic fibers capable of accepting at least one photosensitizer formulation. Further, the one or more embodiments may incorporate at least one photosensitizer which non-exclusively may include known and contemplated photosensitizers including but not limited to all types of methylene blue derivatives and methylene blue itself, chlorophyll derivatives, tetrapyrrole structures, porphyrins, chlorins, bacteriochlorins, phthalocyanines, texaphyrins, prodrugs such as aminolevulinic acids, phenothiaziniums, squaraine, boron compounds, various transition metal complexes, hypericin, riboflavin, curcumin, titanium dioxide, psoralens, tetracyclines, indocyanine green, flavins such as riboflavin, erythrosine, and the like. The one or more embodiments may also include known or contemplated nano-compositions of photosensitizers and photosensitizers linked to a variety of other substances, or utilized in combination with other substances which may improve the photodynamic decontaminating effect. Also, in the one or more embodiments, the fan blade material is coated with known scented oils with known antimicrobial properties such as tea tree oil, lemongrass oil, eucalyptus oil, menthols, peppermint oils, lemongrass oils, orange oils, various aldehydes, phenols, and the like, which may be applied as a spray. Light sources enabling photoactivation include can include, but are not limited to lasers, laser diodes, light emitting diodes, and other semiconductor light sources such as those using quantum dot technology. Fluorescent, incandescent lighting, ambient outdoor light, light from combustion of materials causing flame, are also included in the present disclosure. Moreover, in the one or more embodiments, the light source is comprised of at least one light emitting diode which emits a light spectrum which substantially overlaps the absorption band of at least one photosensitizer, enabling rapid and efficient photoactivation.

Additionally, in the one or more embodiments, the rotating shaft with attached fan blades is comprised of a flexible optical fiber with an outer diameter of 0.1 millimeters to 8.0 millimeters, with a bend radius of 1.0 centimeters. In another embodiment the optical fiber is butted up to at least one light emitting diode, and is able to leak light along its entire length, providing photoactivating light to the fan blades coated with at least one photosensitizer. In yet another of the one or more embodiments, the rotating shaft is 3.0 centimeters to 50.0 centimeters long, and may optionally be in a curved or even a coiled shape, with a bend radius of 5-10 centimeters, or greater.

Further, in the one or more embodiments, the tangential fan housing may be in the shape of a cylinder, with an outer diameter of 1.0 centimeter to 50.0 centimeters or greater, and may encompass a length of 3.0 centimeters to 100.0 centimeters or longer. In yet another of the one or more embodiments, the tangential fan housing is 0.1 millimeter to 10.0 millimeters in thickness.

Also, in one or more of the embodiments, the cylindrical housing coated with at least one photosensitizer can also rotate around an axis.

Further, in the one or more embodiments, the interior of the tangential fan housing is coated with a reflective coating comprised of silver, gold, or aluminum, or a film such as mylar, which reflects photoactivating light back to the fan blade surfaces coated with at least one or more photosensitizers.

In one or more embodiments, the concentration range of at least one photosensitizer can range from 0.1 micromolar to 2000 micromolar, or up to a 5% solution or up to a 75% weight for weight aqueous formulation.

Also, in the one or more embodiments, at least one light source is incorporated into the tangential fan housing. Further, in yet another of the one or more embodiments, at least one non-imaging lens is incorporated into the tangential fan housing that admits photoactivating ambient light into the interior of the housing.

Further, in the one or more embodiments, a substance which can attract water vapor from the atmosphere such as hydroscopic konjac gum may be incorporated into the fan blade surface and interior of the fan assembly housing along with at least one photosensitizer to provide an air cooling adiabatic mechanism, along with pathogen inactivation and killing, with air cooling enabled by air flow over the hydroscopic substance which induces evaporation of the water in the hydroscopic substance.

In the one or more embodiments, a refillable or replaceable reservoir containing at least one photosensitizer formulation is incorporated into the tangential fan housing, which elutes the formulation in a controllable manner onto the fan blades and into the lining of the tangential fan housing. This action renews the photosensitizer that may photobleach over time, which can reduce effective photoactivation from light absorbed by the photosensitizer, and which in turn may reduce the antimicrobial or antitoxin and/or anti-poison action of the photosensitizer.

In the one or more embodiments, a tangential fan housing may incorporate a hinged or removable segment, which permits reapplication of at least one photosensitizer formulation, applied as a film, a powder, or a spray, directly into the interior of the housing, coating the fan blade(s) and the interior of the housing. This action can renew capability of the tangential fan to induce the photoactive disinfection/sanitization/inactivation processes.

In one or more embodiments, the tangential fan housing may be comprised of an optically clear polymer such as, but not limited to, transparent polypropylene, polystyrenes, polycarbonate, polyethylene, or polyesters which can transmit photoactivating light to the interior of the tangential fan housing. Further, in the one or more embodiments, a light source can be positioned external to a light transmissible housing. Also, in another of the one or more embodiments, a light source may be positioned internally within the light transmissible housing.

In one or more embodiments, an ultrasonic motor, which is a type of piezoelectric motor powered by vibration of a stator abutting a rotor, can be utilized to spin the fan blades.

Also, in one or more embodiments, an active powered fan may be used to passively spin a secondary fan proximate and aligned parallel to the main powered fan, using air flow from the spinning powered fan to turn the secondary fan blade. The fan blade(s) surfaces and the inner housing surfaces of the dual housing arrangement may incorporate at least one photosensitizer, enabling two points of photosensitizer contact in sequence to improve the air disinfection capability. Further, the passively driven secondary fan can minimize impedance of air flow from the main powered fan when compared to a conventional filter.

Also, in one or more embodiments, at least two tangential fans are juxtaposed in parallel, with one fan rotating in one direction and another proximate fan rotating in an opposite direction, to increase air contact time with each fan blade and the fan blade housing, with concomitant increased light exposure. In yet one or more of the embodiments, one of the two juxtaposed fans may be larger in diameter, at least 1.5 to 2× or greater in diameter, such that air is ejected at a particular direction tangential to the long axis of the tangential fan assembly, while still providing for a net increase in air contact time with the fan blades and fan blade housing. The counter-rotation scheme essentially permits air recirculation and increases exposure of potentially contaminated air to reactive oxygen species and singlet oxygen by the illuminated photosensitizer(s) coating the fan blades and the inner housing of the fan assembly.

Further, in one or more embodiments, the fan blades of a rotating fan may be of a width of 0.1 millimeter to 2.0 centimeters, spaced apart on a rotating shaft which is comprised of a flexible polymer, housed in a flexible optionally transparent housing which is tube-like in structure, the entire structure able to be bent into a curvilinear shape as desired by a user.

Also, in one or more embodiments, a tangential fan assembly may be configured in a curved shape that partially encircles a hat with a brim, at the junction of the brim with the inferior aspect of the dome of the hat, which contains a slit which permits the flow of air in a direction inferior to the hat brim, creating an air curtain anterior to the face. Further, a zone of disinfected or detoxified or otherwise purified air may be created anterior to the face, enabling inspiration of pathogen, allergen, and toxin free air, while protecting the eye surfaces, nose, mouth, mucous membranes contacting the air stream, and the facial skin from contamination.

In one or more embodiments, a photoactive fabric incorporated into the fan blade(s) and/or fan blade(s) surface is rough, or textured, or contains micro-projections/micro-loops such as may be found in microfiber type of materials in order to maximize the surface area of the fan blade(s) surface which allows for maximal loading of at least one photosensitizer on the fan blade(s) surface which in turn generates increased amounts of reactive oxygen species when exposed to light of the proper waveband or wavelength absorbed by the photosensitizer(s).

In one or more embodiments, a fabric or coating may incorporate at least one or more photosensitizers such as methylene blue at a concentration ranging from 1.0 micromolar to 3,000 micromolar. The photosensitizer may be incorporated using a variety of methods such as heated bath dyeing, sublimation, jet pressure and drying application, heated transfer sheet processing, roller application with heat and pressure, or the like. Further, in one or more embodiments, a photo-linking process for surface attachment of photosensitizers can be used, as well as modifications to the above processes using chemicals such as sodium hydroxide that increase the pH of the solutions, which can increase the photosensitizer uptake into a fabric or coating which is incorporated into the fan blades, and/or fan housing interior.

Unexpectedly, use of one or more of the above embodiments for techniques to apply water soluble photosensitizer (s) such as methylene blue and other hydrophilic or amphiphilic photosensitizers to hydrophobic materials such as polypropylene, or to hydrophobic coatings such as silicones, siloxanes, waxes, acrylics, methylmethacrylates, urethanes, fluorinated compounds, and the like, can lead to aggregation of photosensitizers which is known to reduce singlet oxygen production and reduce antimicrobial efficiency.

Unexpectedly, in one or more embodiments, the known reduction of antimicrobial action by stacking of planar photosensitizers such as methylene blue, leading to dimer, trimer, and greater numbers of "piled" configurations does not occur on the dry, hydrophobic or non-hydrophobic materials and surfaces. Spraying, dipping, wiping, and similar application methods of very high photosensitizer (such as methylene blue and other known or contemplated light activated substances) concentrations in solution at or above 1000 micromolar to hydrophobic surfaces and materials such as polypropylene followed by room temperature or less than 100 degrees F. drying for at least two hours in ambient pressure environments (one atmosphere) unexpectedly leads to successful incorporation and embedding of high concentrations of water soluble or amphiphilic photosensitizers into hydrophobic materials, which teaches away from the prior art/notion that these types of materials such as polypropylene are virtually impossible to dye without special dispersal agents, dye modifications, hydrophobic surface modifications, and extreme temperature and pressures.

The above processes of the one or more embodiments, represent a form of photo-crosslinking of at least one photosensitizer to the hydrophobic coating or material or substance using ambient indoor light, typically less than 50,000 lux, and more often less than 100 lux.

Furthermore, in one or more embodiments, an unexpected benefit of the above photosensitizer incorporation methods and techniques may be reduction of photobleaching phenomenon which occurs from auto-destruction by singlet oxygen, or photodegradation. Photobleaching reduces the antimicrobial action from light absorption by intact photosensitizer molecules, since there are fewer photoactive photosensitizer molecules. The stacking of photosensitizer molecules or monomers creating dimers, trimers, and greater numbers of "piled" molecules (multimers) unexpectedly leads to photobleaching resistance probably due to reduced light adsorption by the less exposed photosensitizer molecules which are in essence protected by light. Despite less net photoactivation processes occurring in the relatively dry state, at comparable concentrations, compared to an aqueous solution, the antimicrobial action remains comparable, which teaches away from the known art. In one or more embodiments, photomicrographic image(s) captured after methylene blue application demonstrate methylene blue multimer aggregates which are unexpectedly highly resistant to photobleaching and yet capable of generating effective antimicrobial singlet oxygen amounts, which teaches away from prior art that dimers, trimers, and multimers are less effective than photosensitizers in solution. In the one or more embodiments, tests comparing the equivalent methylene blue concentrations in monomeric solutions and on hydrophobic materials as multimers such as polypropylene as the hydrophobic material can be performed demonstrating that multimeric photosensitizer multimer formations are effective as antimicrobials.

In the one or more embodiments, pre-treatment of materials may be provided with at least one photosensitizer in solution or in a dry powder state, including techniques such as jet spraying, dipping and nipping, high pressure roller and temperature baths, sublimation, heat transfer sheet, increased pH, photo-crosslinking, and other known dye application processes, followed by spray and/or dipping, and/or wiping applications of at least one photosensitizer in solution, or applied as a dry powder can unexpectedly augment the incorporated photosensitizer concentration and volume on a material or surface, which may be hydrophobic, and not normally able to accept a high photosensitizer or dye concentration, above 1000 micromolar, or even above 50 micromolar.

In the one or more embodiments, a flexible or conformable tangential fan may be affixed or incorporated into a pair of eye glasses, goggles, a headband, or into a helmet (positioned anterior to the face and head), or related headgear and/or eyewear. In the one or more embodiments, the flexible or conformable tangential fan can be configured as a necklace shape and worn around the neck, with the airstream directed in a superior or upward direction toward the face of the user. In these relatively thin embodiments, the fan blade housing diameter may be 5.0 mm or less, and the fan shaft can be optionally flexible and conformable into a curved shape, and the fan shaft driving mechanism and battery may be incorporated into a frame of eye glasses, goggles, headband, helmet, and/or a necklace. In these one or more embodiments, a rotating shaft with attached fan blades may be driven by a miniature electric motor which is powered by a rechargeable battery.

In one or more embodiments, one or more fan blades may be replaceable, or may be anchored in place on a rotating polymeric or metallic shaft using epoxies, cyanoacrylates, polyurethanes, or other known bonding agents and glues. In the one or more embodiments, the flexible rotating shaft may be comprised of nitinol. Further, in the one or more embodiments, the fan blade rotation speed can be variable and adjustable, which can optimize contaminated air contact time for decontamination/treatment and expelling parameters for maximal inhalation of decontaminated/treated air. Further, in the one or more embodiments, the rotating fan speed may be alternately increased and decreased, to provide for more photo-disinfection/photoinactivation time at slower rotation speeds, followed by more rapid rotation speeds which ejects the disinfected/purified air at a faster rate, increasing the probability of a user inhaling the photo-processed air.

In one or more embodiments, a series of experiments may be performed using aerosolized microbes, smoke, and other noxious airborne substances and organisms to determine optimal fan speeds, photosensitizer(s) concentrations, air dwell time within a fan assembly housing, and the like, by performing appropriate assays demonstrating decontamination and/or breakdown or destruction of noxious airborne substances, particles, or pathogens or surrogate microbes. Further, in the one or more embodiments, a wetting agent such as water applied or captured from the air to the fan blades to facilitate capture and decontamination and/or breakdown of noxious airborne substances or microbes which can be dissolved or attracted to the fan blade surfaces for photoinactivation by light and at least one photosensitizer disposed on the fan blade(s) surface or inner surface of the fan assembly housing, or within an incorporated nozzle or air flow director or tube like air flow director.

In one or more embodiments, at least one of known phase-change materials including polymers, salts, and other known chemicals, known to change from solid-liquid and vice versa, may be optionally part of this disclosure. These materials may be microencapsulated, and can be incorporated into the fan blades and/or the tangential fan housing, to provide heated or cooled expelled purified air as desired, for hot and cold environments. Further, in the one or more embodiments, known phase change materials may be incorporated into the substance of the fan blade(s). Also, in the one or more embodiments, phase change materials may non-exclusively include waxes such as eicosane, octadecane, nonadecane, heptadecane, and hexadecane, which are known to be microencapsulated for incorporation into fan blade(s). Other phase change substances include paraffin wax, carboxylic acids, Glauber's salt which is sodium sulfate decahydrate, and calcium chloride hexahydrate. Matrix coating using coating substances such as polyurethanes, acrylics, and the like, various knifing techniques, padding techniques, dip and transfer coating, gravure processing, and foam dispersion using polyurethanes, as examples of application and incorporation methods and techniques known in the textile and fabric manufacturing industry, can be used to coat fan blade(s).

DRAWING DESCRIPTIONS

Figure 1A:
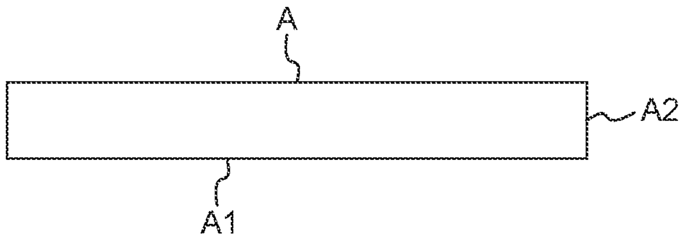
FIG. 1A depicts elongate shaped fan blade A, with a width A1 that is greater than its height A2, which is comprised of a polymer, which may be a synthetic material, and/or a natural fiber.
Figure 1B:
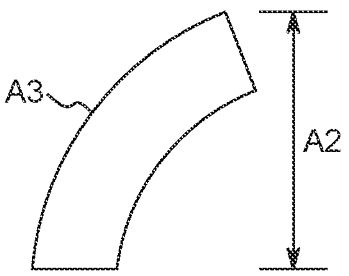
FIG. 1B shows a side view of fan blade A3 as curved in its height A2 dimension.
Figure 1C:
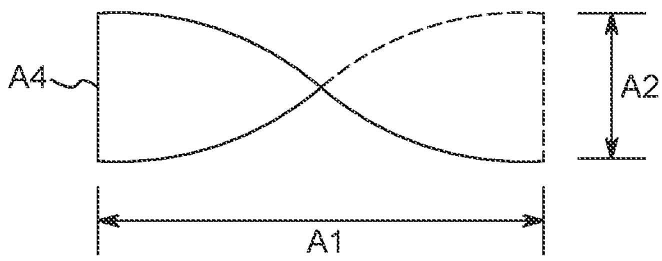
FIG. 1C illustrates fan blade A4 in the shape of a screw or auger, longer in width A1 than height A2.
Figure 1D:
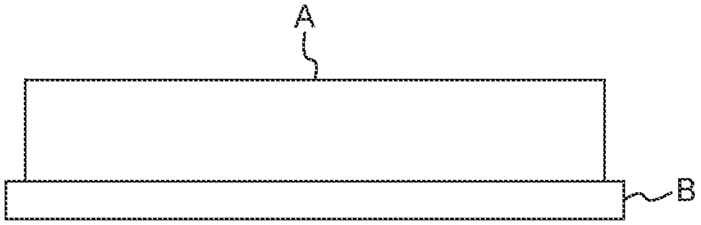
FIG. 1D shows a polymeric or metallic elongate shaft B, to which fan blade A is affixed with epoxy, resin, or glue.
Figure 1E:
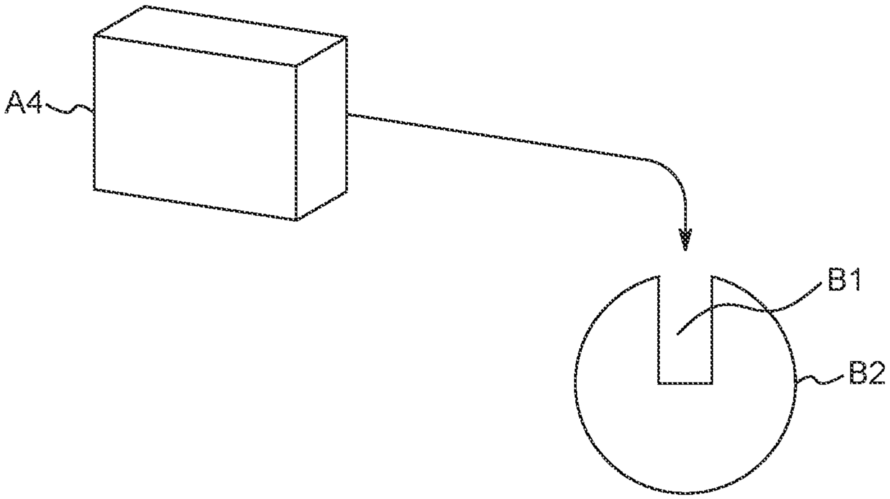
FIG. 1E depicts replaceable blade A4 shown in a position for placement into slot B1 shown in a side view in elongate shaft B2 also shown in side view.
Figure 1F:
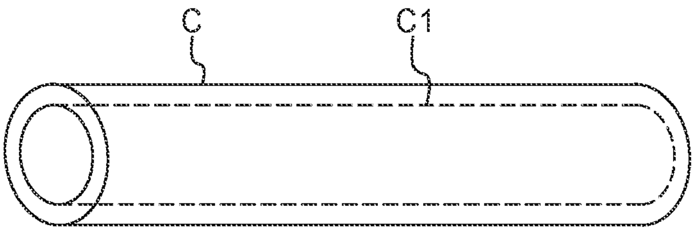
FIG. 1F shows tangential fan housing C in an elongate configuration, lined with coating C1, which may be comprised of at least one photosensitizer and/or phase change material/and or reflective material.
Figure 1G:
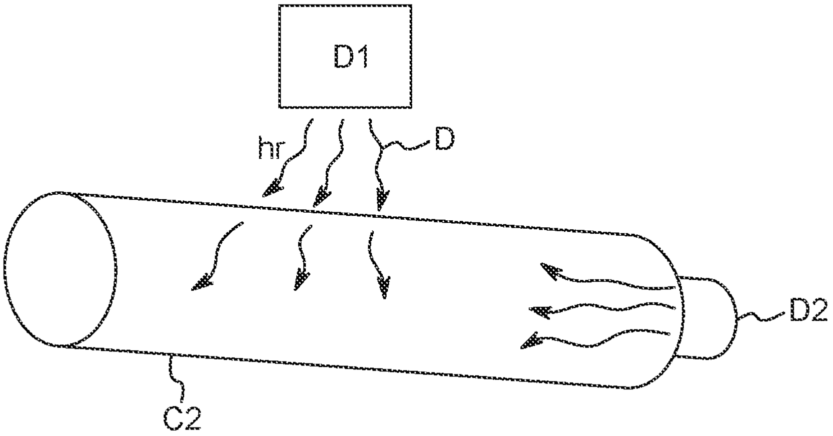
FIG. 1G depicts tangential fan housing alternative C2 is comprised of a transparent material, admitting light D from external light source D1. Incorporated light source D2 which is optionally at least one light emitting diode, can also supply light D to interior of tangential fan housing C2.
Figure 1H:
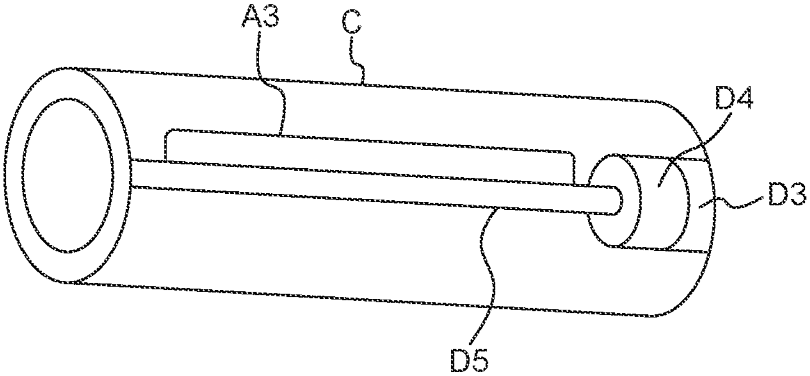
FIG. 1H shows rechargeable battery D3 powers electric motor D4 incorporated into tangential fan housing C which drives rotating shaft D5 which rotates attached fan blade A3.
Figure 1I:
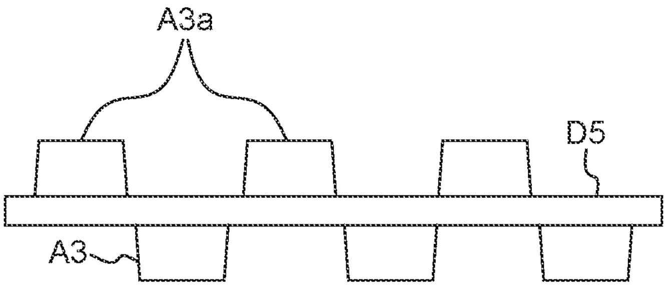
FIG. 1I depicts A3*a* as a representation of a segmented multiple fan assembly attached to rotating shaft D5.
Figure 1J:
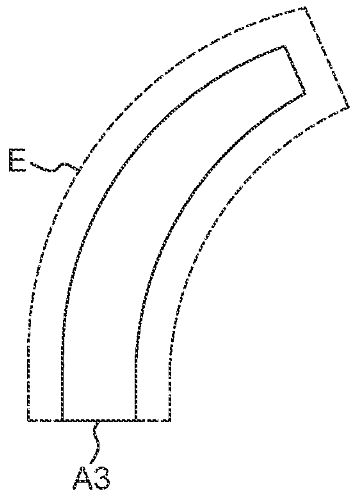
FIG. 1J shows a side view of curved fan blade A3 coated with at least one photosensitizer and/or phase change material E.
Figure 1K:
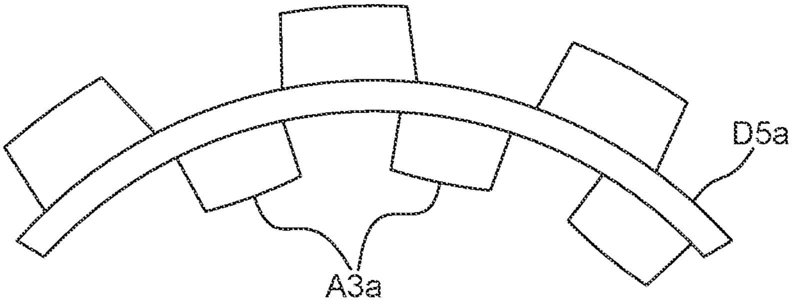
FIG. 1K depicts a side view of a curved shape of rotating shaft D5*a* that is attached to curved fan blade A3*a*.
Figure 2A:
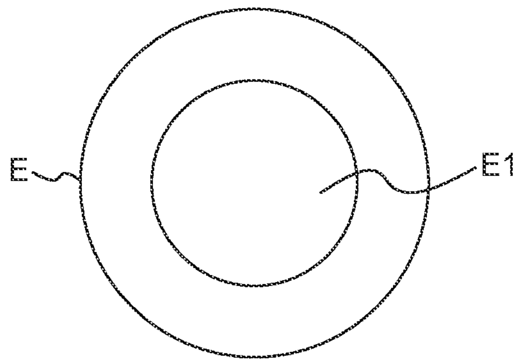
FIG. 2A shows microencapsulated phase change material E1 surrounded by microcapsule E, which ranges in outer diameter from 1.0-500.0 microns.
Figure 2B:
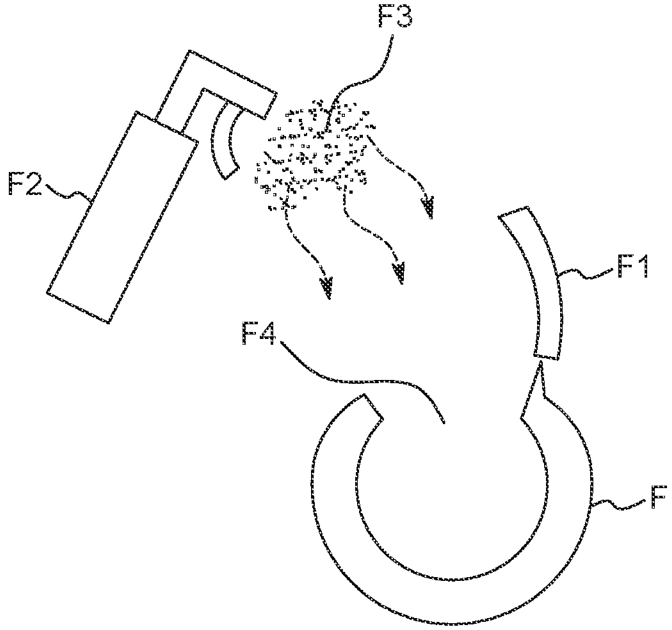
FIG. 2B depicts spray bottle F2 delivering photosensitizer aerosol F3 into the interior of housing F through open hinged cover F1 into opening F4.
Figure 3A:
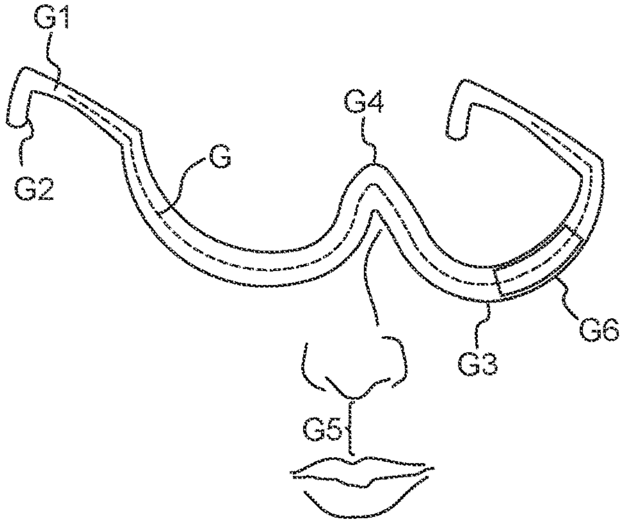

FIG. 3A shows dashed lines G which represent a rotatable fan shaft powered by battery/driver mechanism G1 incorporated into glasses temple G2. Furthermore, rotating shaft G with attached fan blade(s) G6 which incorporates at least one photosensitizer, is contained in housing G3 which constitutes the inferior aspect of the eye glasses frame G4 which includes temple G2. The opening in housing G3 where disinfected air is ejected is located at the inferior aspect of housing G3, enabling the disinfected air stream to be directed toward mouth and nose G5.

Figure 3B:
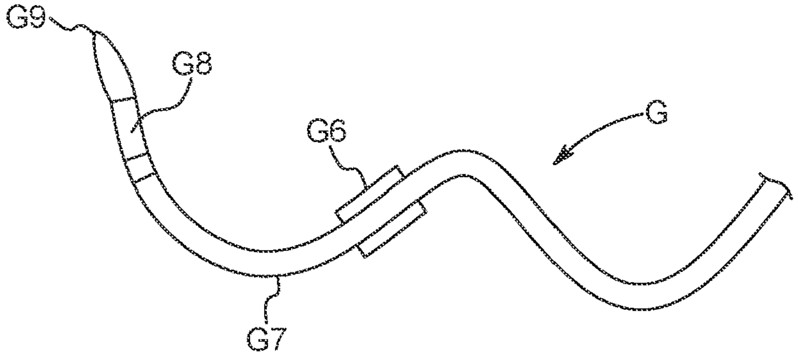

FIG. 3B illustrates fan shaft G is comprised of an optical fiber G7, which is butted up to light emitting diode array G8 which emits light that is powered by rechargeable battery G9. Light which leaks from optical fiber G7 along its length serves to photoactivate at least one photosensitizer incorporated into fan blade(s) G6, attached along the length of optical fiber G7.

Figure 3C:
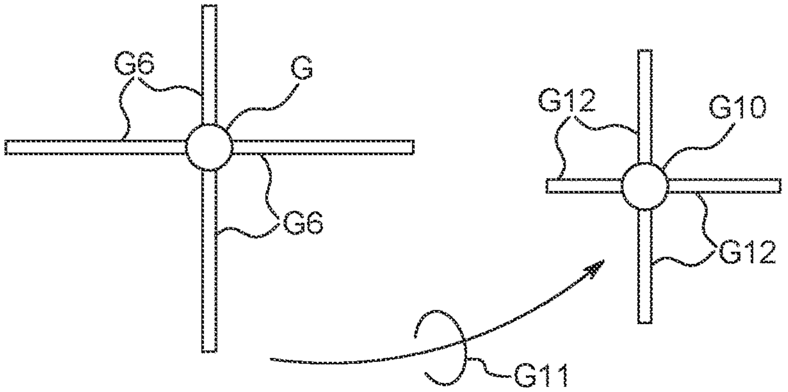

FIG. 3C shows a cross section of fan shaft G with attached fan blades G6 proximate and in parallel to secondary fan shaft G10, which is rotated by air flow G11 from powered fan shaft G turning fan blades G6 pushing against secondary fan blades G12.

What is claimed as new and desired to be protected by Letters Patent of the United States is:

1. A device, comprising:

one or more fan blades;

a rotatable fan shaft;

an eye glass shaped frame that includes a hollow cavity and having an opening arranged to eject a flow of air towards one or more of a mouth or a nose of a user when the frame is worn on their face, wherein the rotatable shaft and one or more fan blades are integrated within the hollow cavity;

a photosensitizer formulation that is disposed on one or more of the one or more fan blades, the rotatable fan shaft, and an interior surface of the hollow cavity of the frame, wherein the photosensitizer formulation comprises one or more organic photosensitizers;

a container that is configured as a reservoir for the photosensitizer formulation, wherein the container is arranged to elute the photosensitizer formulation into the hollow cavity over time to maintain an amount of the photosensitizer formulation disposed on the one or more of the fan blade, the rotatable fan shaft, and the interior surface of the hollow cavity; and wherein the device generates the flow of ejected air towards an exterior surface of the user's face that includes the mouth and nose, and wherein the one or more organic photosensitizers of the photosensitizer formulation are activated by light to emit singlet oxygen into the flow of air to inactivate airborne pathogens that mix with the flow of air, and wherein the emission of singlet oxygen also inactivates pathogens that are in contact with one or more portions of the exterior surface, the one or more fan blades, the rotatable fan shaft, and the interior surface of the hollow cavity of the frame.

2. The device of claim 1, further comprising:

one or more secondary fan blades and a rotatable secondary fan shaft that are operable to relay the directed flow of air towards the exterior surface.

3. The device of claim 2, wherein the photosensitizer formulation is disposed on the one or more secondary fan blades and the secondary rotatable fan shaft; and wherein the light activates the photosensitizer formulation disposed on the one or more secondary fan blades and the rotatable secondary fan shaft to emit singlet oxygen into the flow of air.

4. The device of claim 1, wherein the one or more fan blades of the device form a screw shape.

5. The device of claim 1, wherein the rotatable fan shaft is configured to include one or more curved shapes.

6. The device of claim 1, wherein activating the photosensitizer further comprises:

activating one or more portions of the photosensitizer formulation that is disposed on the exterior surface.

7. The device of claim 1, wherein at least one of the one or more fan blades is disposed contiguously along a length of the rotatable fan shaft.

8. The device of claim 1, wherein a plurality of the fan blades are disposed intermittently along a length of the rotatable fan shaft.

9. The device of claim 1, wherein the eyeglass shaped frame further comprises:

a frame for one of a pair of eye glasses or goggles to enclose the device; and wherein the activated photosensitizer formulation emits singlet oxygen in the flow of air that is emitted from the frame towards the face of the user.

10. The device of claim 1, further comprising:

one or more ports in the eyeglass shaped frame that are operable to reapply the photosensitizer formulation to the one or more of the one or more fan blades, the rotatable fan shaft, and the interior surface of the eyeglass shaped frame.

11. The device of claim 1, further comprising:

one or more antimicrobial formulations that are disposed on the one or more of the one or more fan blades, the rotatable shaft or the interior surface of the eyeglass shaped frame, wherein the one or more antimicrobial formulations include one or more of scented oils comprising tea tree oil, lemongrass oil, eucalyptus oil, menthol oil, peppermint oil, orange oil, aldehyde, and phenol.

12. The device of claim 1, further comprising:

one or more light sources to emit the light for activation of the photosensitizer formulation, wherein the one or more light sources include one or more of a laser, a laser diode, a light emitting diode, a fluorescent lamp, and an incandescent lamp and wherein one or more portions of the one or more light sources emit a light spectrum that provides an overlap of an absorption band of the photosensitizer formulation.

13. The device of claim 1, wherein the one or more organic photosensitizers further comprise at least methylene blue.

14. The device of claim 1, wherein the eyeglass shaped frame further comprises:

one or more portions of the eyeglass shaped frame that include a transparent material, wherein the one or more transparent portions are arranged to admit light from an external source onto the photosensitizer formulation disposed on the one or more of the interior surface of the eyeglass shaped frame, the rotatable fan shaft, or the one or more fan blades.

* * * * *